US009964555B2

(12) United States Patent
Girardey et al.

(10) Patent No.: US 9,964,555 B2
(45) Date of Patent: May 8, 2018

(54) FIELD DEVICE FOR DETERMINING OR MONITORING A PHYSICAL OR CHEMICAL PROCESS VARIABLE IN AUTOMATION TECHNOLOGY

(75) Inventors: Romuald Girardey, Blotzheim (FR); Michael Hubner, Bodum (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 921 days.

(21) Appl. No.: 14/238,589

(22) PCT Filed: Jul. 18, 2012

(86) PCT No.: PCT/EP2012/064042
§ 371 (c)(1),
(2), (4) Date: Feb. 12, 2014

(87) PCT Pub. No.: WO2013/026631
PCT Pub. Date: Feb. 28, 2013

(65) Prior Publication Data
US 2014/0214366 A1    Jul. 31, 2014

(30) Foreign Application Priority Data
Aug. 19, 2011 (DE) .................. 10 2011 081 268

(51) Int. Cl.
*G01N 35/00* (2006.01)
*H04B 5/00* (2006.01)

(52) U.S. Cl.
CPC ....... *G01N 35/00871* (2013.01); *H04B 5/005* (2013.01); *H04B 5/0031* (2013.01); *H04B 5/0081* (2013.01)

(58) Field of Classification Search
CPC ............ G01N 35/00871; H04B 5/0031; H04B 5/005; H04B 5/0081; H04B 5/0093; H01L 23/645; H01L 25/0657; G05B 23/0289
See application file for complete search history.

(56) References Cited

U.S. PATENT DOCUMENTS 5,867,535 A * 2/1999 Phillips .................... G01S 1/04
375/295
2008/0284552 A1   11/2008 Lim et al.
(Continued)

FOREIGN PATENT DOCUMENTS

DE        102010002346 A1   4/2011
WO            8601093 A1    2/1986
(Continued)

OTHER PUBLICATIONS

Nov. 22, 2011 German Search Report, German Patent Office, Munich, Germany.
(Continued)

*Primary Examiner* — Manuel L Barbee
(74) *Attorney, Agent, or Firm* — Bacon & Thomas, PLLC

(57) ABSTRACT

A field device for determining or monitoring a physical or chemical process variable in automation technology, comprising at least one transmitting/receiving element, wherein an FPGA component is provided, the transmitting/receiving element is configured in the form of a spiral from existing internal connecting lines of the FPGA component, and the spiral of the transmitting/receiving element transmits data inductively to a second transmitting/receiving element in the form of a spiral.

7 Claims, 9 Drawing Sheets

(56) References Cited

U.S. PATENT DOCUMENTS

2009/0218701 A1* 9/2009 Rofougaran .......... H01L 23/645
                                                    257/778
2010/0069000 A1   3/2010 Nakagawa
2011/0087460 A1* 4/2011 Girardey ................ G05B 9/02
                                                    702/182

FOREIGN PATENT DOCUMENTS

WO    2008046694 A1    4/2008
WO    2013026631 A1    2/2013

OTHER PUBLICATIONS

Aug. 4, 2011 Wikipedia search of Field-programmable gate array; URL: http://en.wikipedia.org/w/index.php?title=Field-programmable_gate_array&oldid=442996964.
Sep. 12, 2012 International Search Report, EPO, The Netherlands.

* cited by examiner

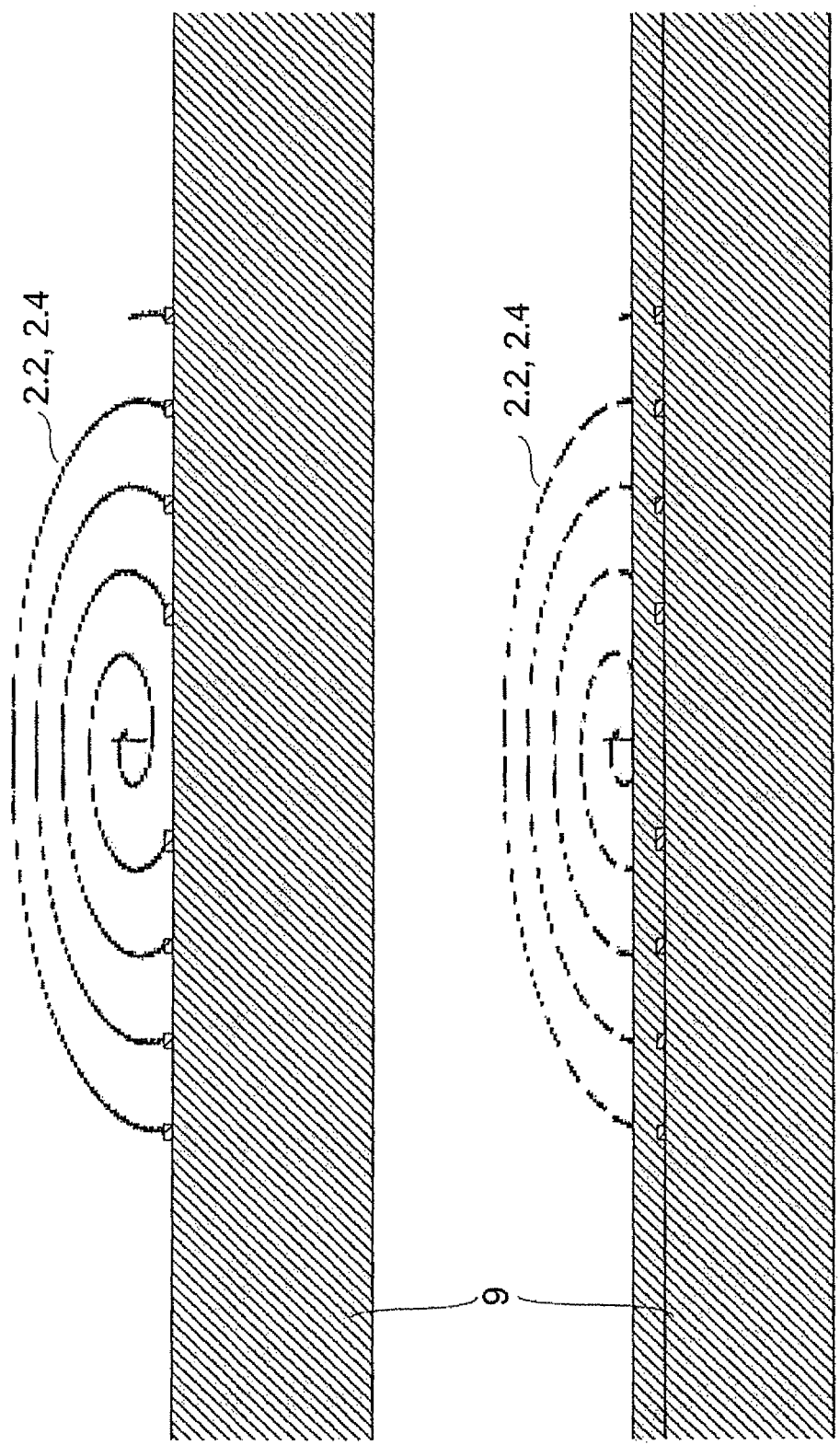

FIELD DEVICE FOR DETERMINING OR MONITORING A PHYSICAL OR CHEMICAL PROCESS VARIABLE IN AUTOMATION TECHNOLOGY

TECHNICAL FIELD

The invention relates to a field device for determining or monitoring a physical or chemical process variable in automation technology, including an apparatus for inductive transmitting and/or receiving of data.

BACKGROUND DISCUSSION

In automation technology, data transmission often occurs via electrical current circuits, which are galvanically isolated from one another, respectively galvanically decoupled. Since, in the case of galvanically isolated connections, electrical potentials are isolated from one another, one speaks also of potential-free connections. Important is the application of galvanically isolated, electrical current circuits especially in field devices, such as sensors, actuators, valves, etc., in explosion endangered areas.

A known method for data transmission involves the so-called print transformer. In the case of print, or also spiral or planar, transformers, used as transformer are two spiral shaped, conductive traces arranged lying opposite one another in or on a circuit board. Transmission of the data occurs via inductive coupling, whereby galvanic isolation is assured. A corresponding solution is disclosed, for example, in U.S. Pat. No. 7,852,186 B2.

Print transformers are often also applied in integrated circuits. They can be integrated relatively simply into the metal plies.

SUMMARY OF THE INVENTION

An object of the invention is to provide for galvanically isolated data transmission within a circuit implemented on an FPGA.

The object is achieved by features including that at least one transmitting/receiving element in the form of a spiral is implemented on an FPGA (Field Programmable Gate Array) component, wherein the spiral is configured from internal connecting lines of the FPGA component. The spiral of the transmitting/receiving element transmits the data inductively to a second transmitting/receiving element in the form of a spiral. The FPGA component is either a one-time configurable FPGA (antifuse FPGA), a reconfigurable, flash FPGA or a dynamically, respectively partially dynamically, thus during runtime, reconfigurable FPGA. A field device, which contains a partially dynamically reconfigurable FPGA is described in detail in Published International Patent Application No. WO 2008/046696 A2. The content of such patent application is to be included in the disclosure of the present patent application.

The spiral can have any shape. Especially, the spiral can have a round or an angular shape. Moreover, the second spiral can be located on the same or another FPGA component, or provided on any component offset from the FPGA component, e.g. a circuit board offset from the FPGA component.

An especially advantageous embodiment of the field device of the invention provides that the spiral is configured from connecting lines arranged in a plurality of connecting line planes of the FPGA component. Thus, it is quite usual that FPGA components have 12 plies of connecting line planes.

Furthermore, it is provided that the at least one spiral of the first transmitting/receiving element is configured permanently on the FPGA component. Alternatively, it is provided that the at least one spiral of the first transmitting/receiving element is dynamically reconfigurable on the FPGA component.

The field device of the invention is especially advantageous when it is applied for use in an area having an increased safety level. For this, at least a first portion and a second portion are provided on the FPGA component. In each portion, a digital measuring path is partially dynamically reconfigurable, wherein the measuring path is composed of a plurality of software based and/or hardware based, function modules.

Moreover, a control/evaluation unit is provided, which partially dynamically reconfigures the function modules in the measuring paths, respectively in the portions, as a function of a defined, safety-critical application, so that the field device meets a required safety standard. A field device applicable in a safety-critical application is described in Published International Patent Application No. WO 2009/062954 A1. Provided in such patent application is a field device for determining or monitoring a process variable in process automation. The field device is composed of a sensor, which works according to a defined measuring principle, and a control/evaluation unit, wherein the control/evaluation unit conditions and evaluates along at least two equal valued measuring paths the measurement data delivered by the sensor as a function of a safety standard required in the respective safety-critical application. In such case, the control/evaluating unit is embodied at least partially as a reconfigurable logic chip having a plurality of partially dynamically reconfigurable function modules. The control/evaluation unit configures the function modules in the measuring paths as a function of the respectively defined, safety-critical application, such that the field device is designed corresponding to the required safety standard.

Especially, it is provided in this connection that the two portions are isolated from one another by a spacing. Preferably, the spacing is so embodied that a potential isolation is achieved between the portions in such a manner that a temperature- and/or a voltage change in one of the portions has no influence on the neighboring portion, respectively neighboring portions, and that, in the case of a defect, no connection occurs between the portions. Moreover, it is provided that the control/evaluation unit is configured permanently in a portion of the FPGA component.

Various embodiments of an FPGA component applicable in connection with the invention are described in Published International Patent Application No. WO 2011/023469 A2; in German Patent No. DE 10 2010 002346 A1 and in the not pre-published German Patent No. DE 10 2919 943 706.9, filed 28 Jul. 2010, respectively in the corresponding U.S. Provisional Application No. 61/344,438, filed 22 Jul. 2010. The disclosures of the cited applications are to be included in the disclosure of the present patent application.

In connection with the field device of the invention, it is advantageous when a transmitting/receiving element in the form of a spiral is associated with each measuring path, respectively each portion. This assures the required electrical isolation.

BRIEF DESCRIPTION OF THE DRAWINGS

The invention will now be explained in greater detail based on the appended drawing, the figures of which show as follows:

FIG. 9 is preferred arrangements of two transmitting/receiving elements, one on, and one in, a circuit board.

DETAILED DISCUSSION IN CONJUNCTION WITH THE DRAWINGS

Figure 1:
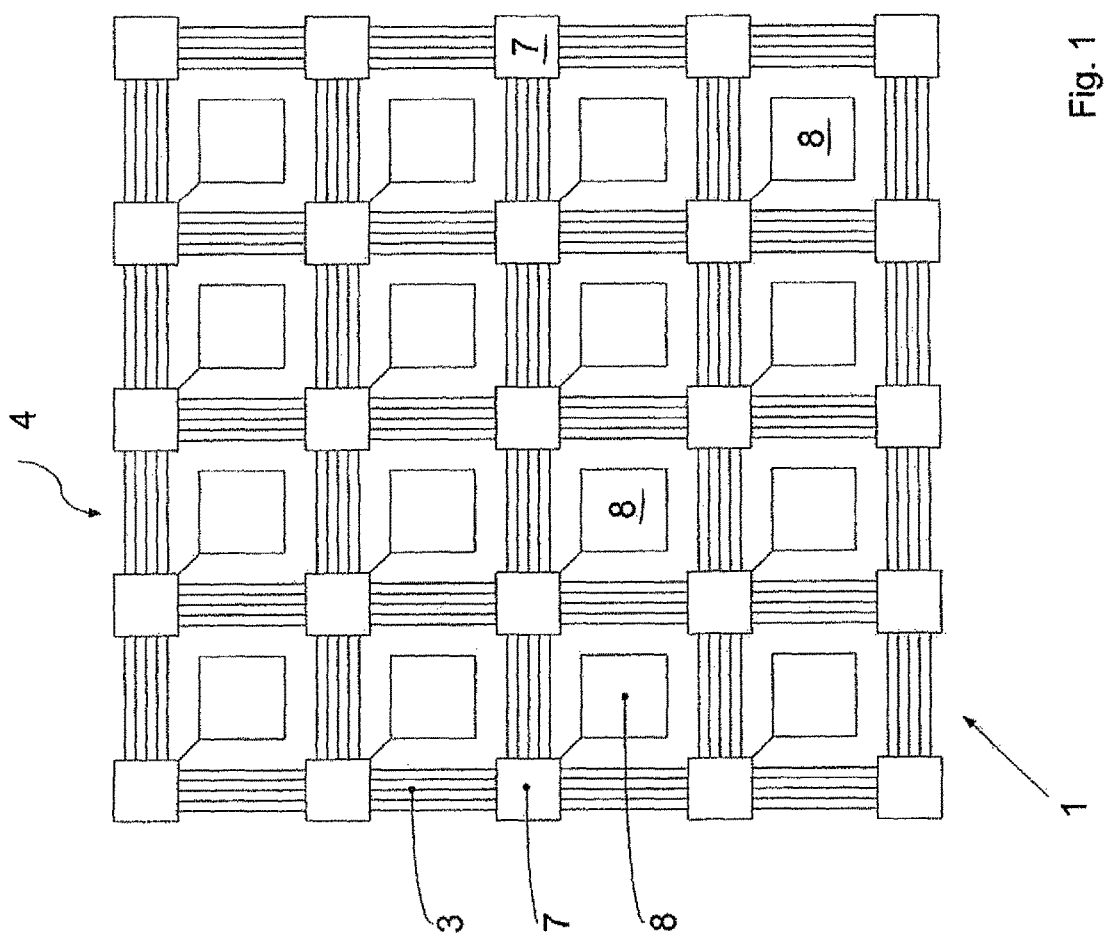
FIG. 1 is a plan view of a section of an FPGA component.

FIG. 1 shows a plan view of a section of an FPGA component 1. An FPGA component 1 is composed usually of a plurality of connecting line planes 4 arranged parallel to one another and a transistor plane. The lowest plane is the transistor plane. It includes the configurable logic chips 8 and the configurable switch matrices 7. The overlying planes are the connecting line planes 4 with connecting lines 3 of various lengths between the different switch matrices 7. By corresponding connecting of the logic chips 8, the required function modules (not separately presented in FIG. 1, but described e.g. in WO 2009/062954 A1) can preferably be partially dynamically reconfigured on the FPGA component 1. The configuring occurs via a control/evaluation unit, which is not separately presented in FIG. 1. Usually, the control/evaluation unit is permanently configured on the FPGA.

Figure 2:
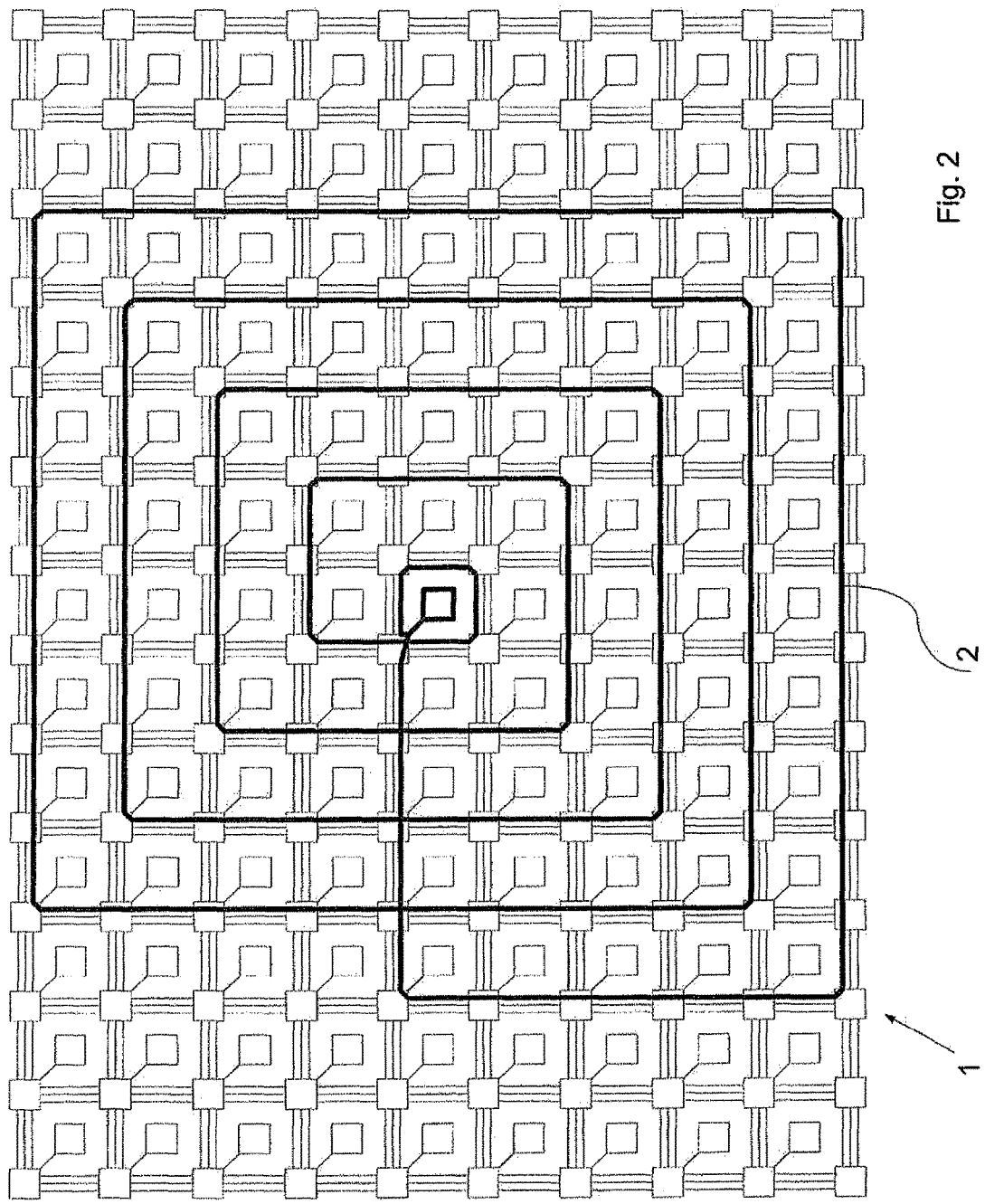
FIG. 2 is a spiral embodied as a transmitting/receiving element on the section of the FPGA component.

FIG. 2 shows a spiral embodied according to the invention as a transmitting/receiving element 2 on the FPGA component 1. The spiral of the transmitting/receiving element 2 is either configured permanently on the FPGA component 1, or the spiral of the transmitting/receiving element 2 is dynamically or partially dynamically reconfigurable on the FPGA component 1. The spiral can—as already mentioned—have any shape.

Figure 3:
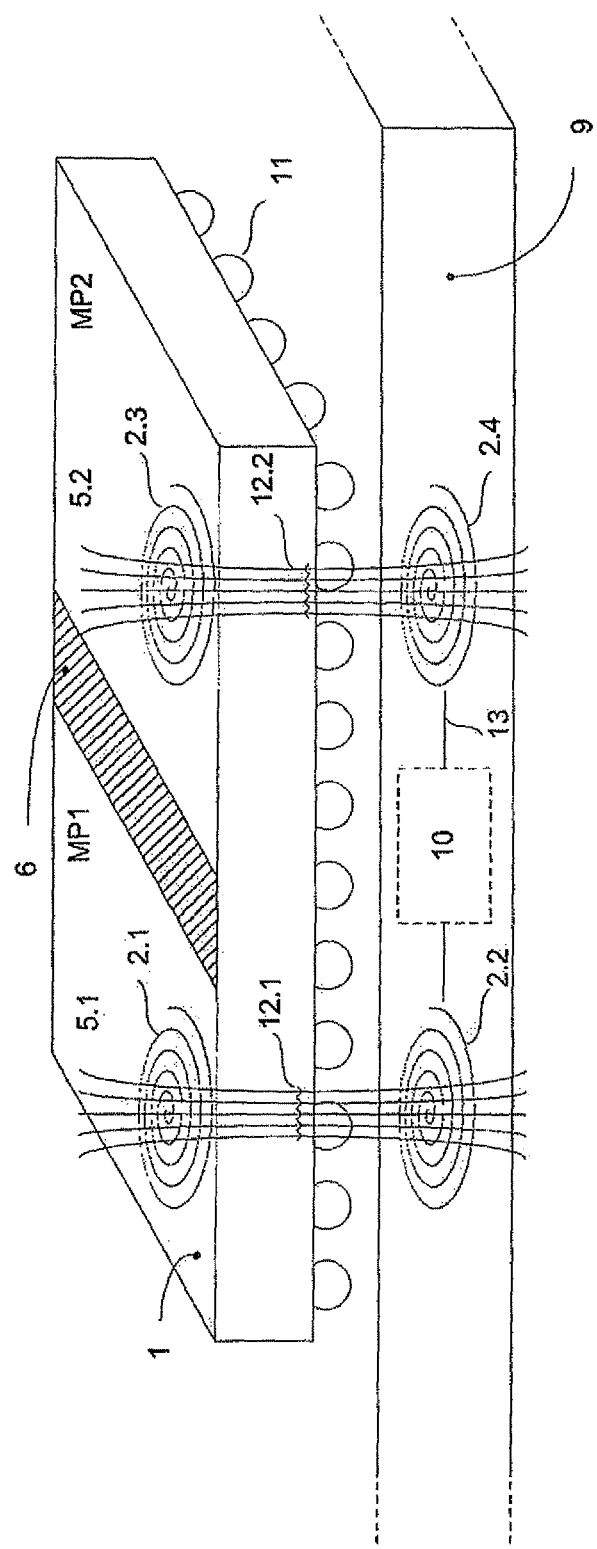
FIG. 3 is a perspective view of a first embodiment of the FPGA component of the invention showing the magnetic field lines.
Figure 4:
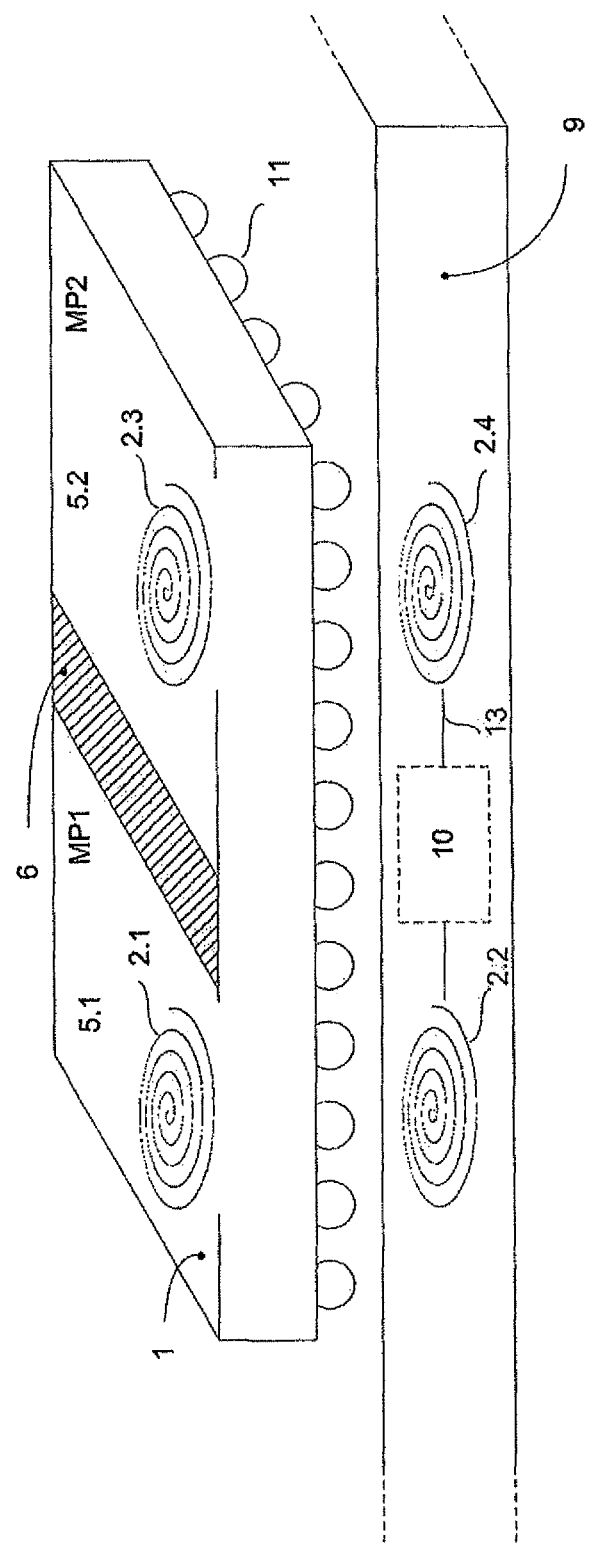
FIG. 4 is the embodiment of FIG. 3 without the magnetic field lines.

FIG. 3 shows a perspective view of a first embodiment of the FPGA component of the invention 1 showing the magnetic field lines 12.1, 12.2. In FIG. 4, the magnetic field lines 12.1, 12.2 are omitted.

The FPGA component 1 includes a first portion 5.1 and a second portion 5.1, wherein in each portion 5.1, 5.2 a digital measuring path MP1, MP2 is partially dynamically reconfigured. To this end, a plurality of software based and/or hardware based function modules, which are not separately presented in FIG. 3, are configurable in each digital measuring path MP1, MP2.

Also provided in FIG. 3 but likewise not separately shown is a control/evaluation unit, which partially dynamically reconfigures the function modules in the measuring paths MP1, MP2, respectively in the portions 5.1, 5.2, as a function of a defined, safety-critical application, so that the field device meets a required safety standard. The individual portions 5.1, 5.2 are isolated from one another by the spacing 6, wherein the spacing 6 is so embodied that a potential isolation is achieved between the portions 5.1, 5.2. This potential isolation prevents that a temperature- and/or a voltage change in one of the portions 5.1, 5.2 can influence the neighboring portion 5.2, 5.1 and also avoids a connection between the portions 5.1, 5.2 in the case of a defect.

The FPGA component 1 is connected with the circuit board 9 via a contacting layer 11. Arranged in or on the circuit board 9 are two transmitting/receiving elements 2.2, 2.4. These correspond to the transmitting/receiving elements 2.1, 2.3 on the FPGA component 1, so that an inductive coupling takes place between the transmitting/receiving elements 2.1, 2.3; 2.2, 2.4. Shown in FIG. 3 are the corresponding magnetic field lines 12.1, 12.2 extending between the respectively corresponding transmitting/receiving elements 2.1, 2.3; 2.2, 2.4.

Data transmission between the two mutually galvanically isolated measuring paths MP1, MP2 occurs via the two transmitting/receiving elements 2.1, 2.3, the electrical connection 13 between the transmitting/receiving elements 2.2 and 2.4 and the two transmitting/receiving elements 2.4, 2.3. A driver 10, respectively an amplifier, is provided arranged between the two transmitting/receiving elements 2.2, 2.4 in or on the circuit board 9 for amplifying the transmitted signals.

Figure 5:
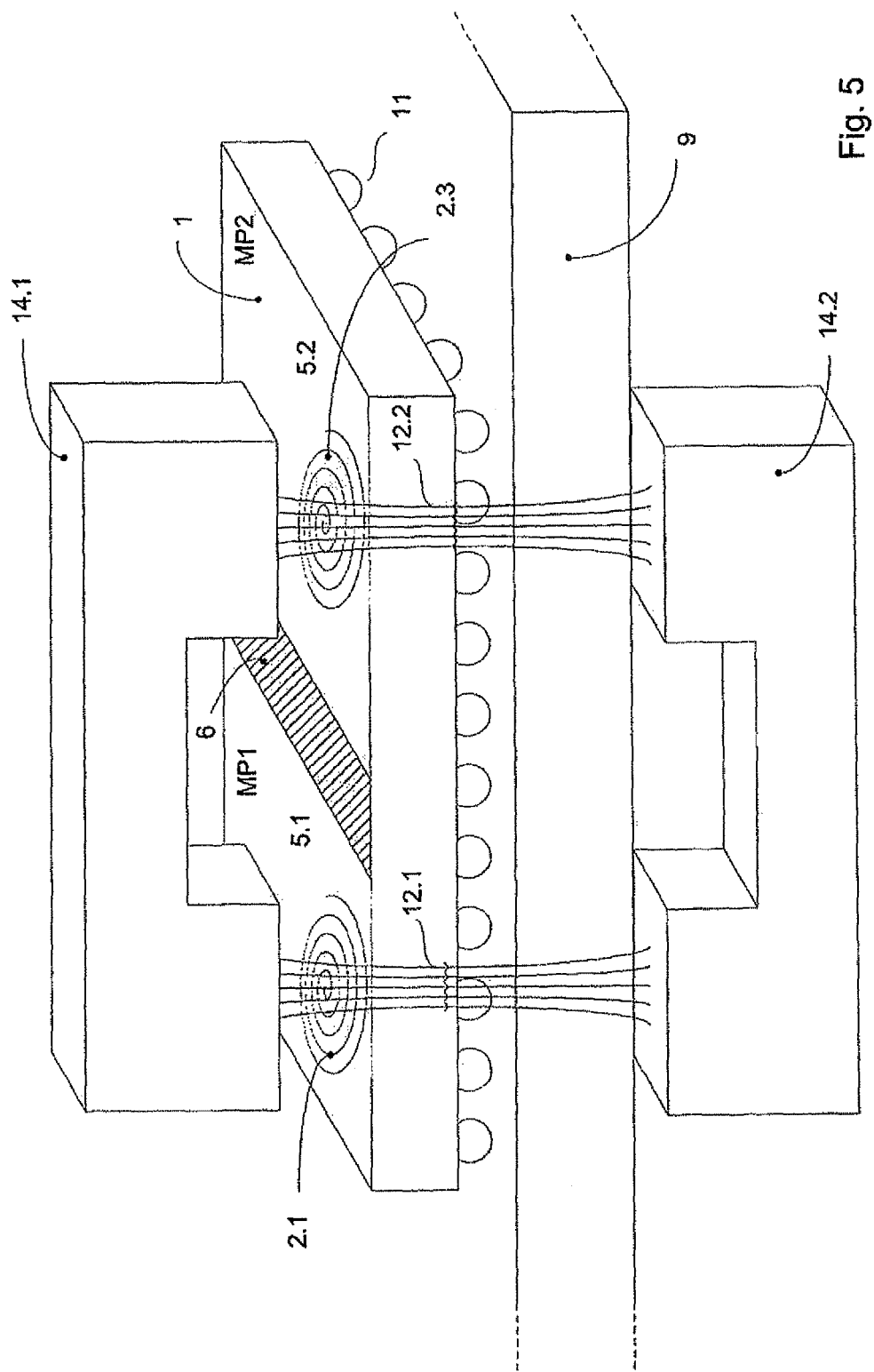
FIG. 5 is a perspective view of a second embodiment of the FPGA component of the invention showing the magnetic field lines.
Figure 6:
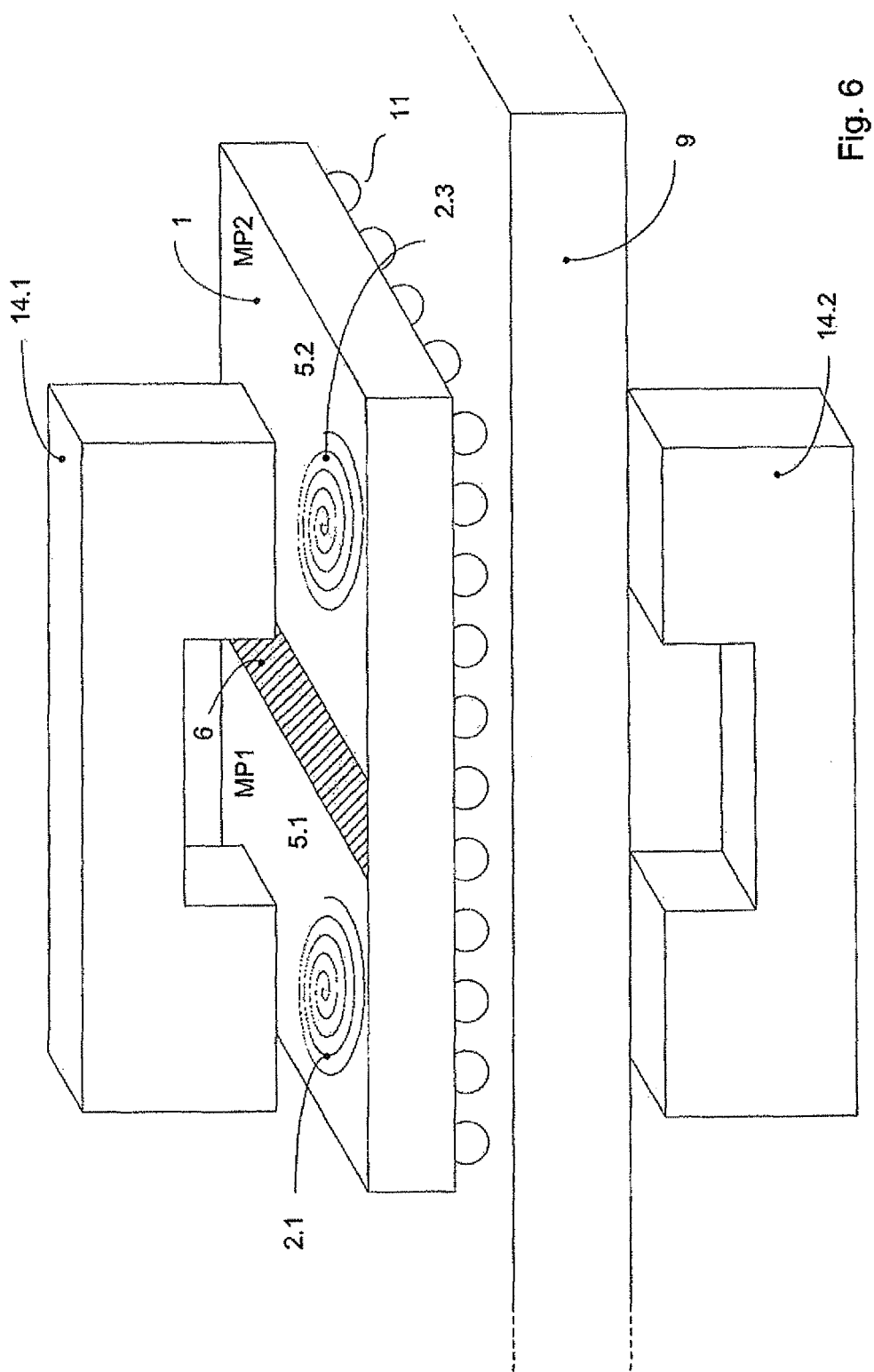
FIG. 6 is the embodiment of FIG. 5 without the magnetic field lines.

FIG. 5 shows a perspective view of a second embodiment of the FPGA component of the invention 1 showing the magnetic field lines 12.1, 12.2. In FIG. 6, the magnetic field lines 12.1, 12.2 have been omitted.

In the case of this embodiment, the inductive data transmission between the two galvanically isolated portions 5.1, 5.2, respectively the measuring paths MP1, MP2, occurs via magnetic core 14.1, 14.2 arranged above and below the circuit board 9 with secured FPGA component 1. The cores 14.1, 14.2 are preferably manufactured from ferrite and bundle and strengthen the magnetic field lines 12.1, 12.2.

Figure 7:
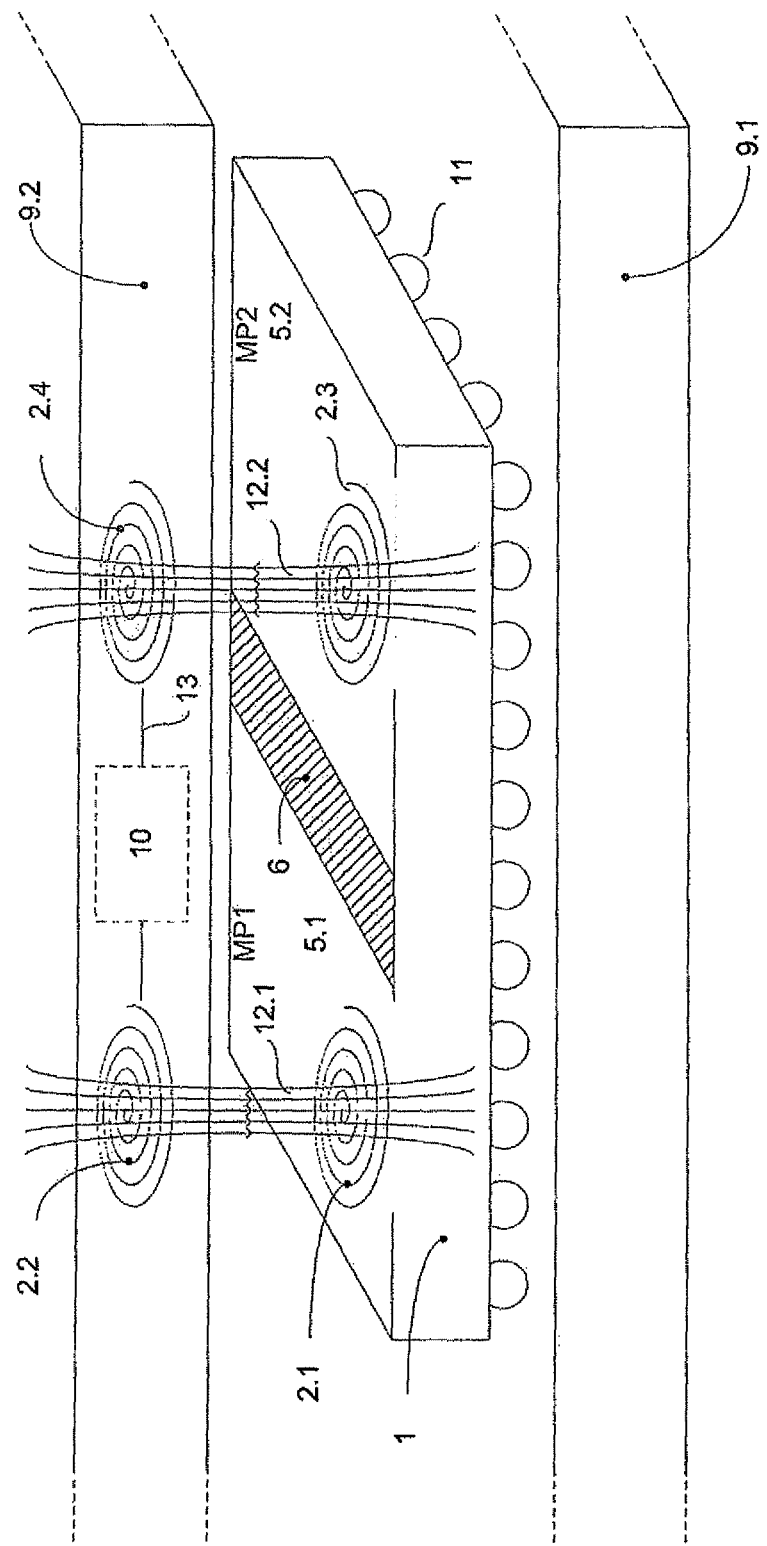
FIG. 7 is a perspective view of a third embodiment of the FPGA component of the invention showing the magnetic field lines.
Figure 8:
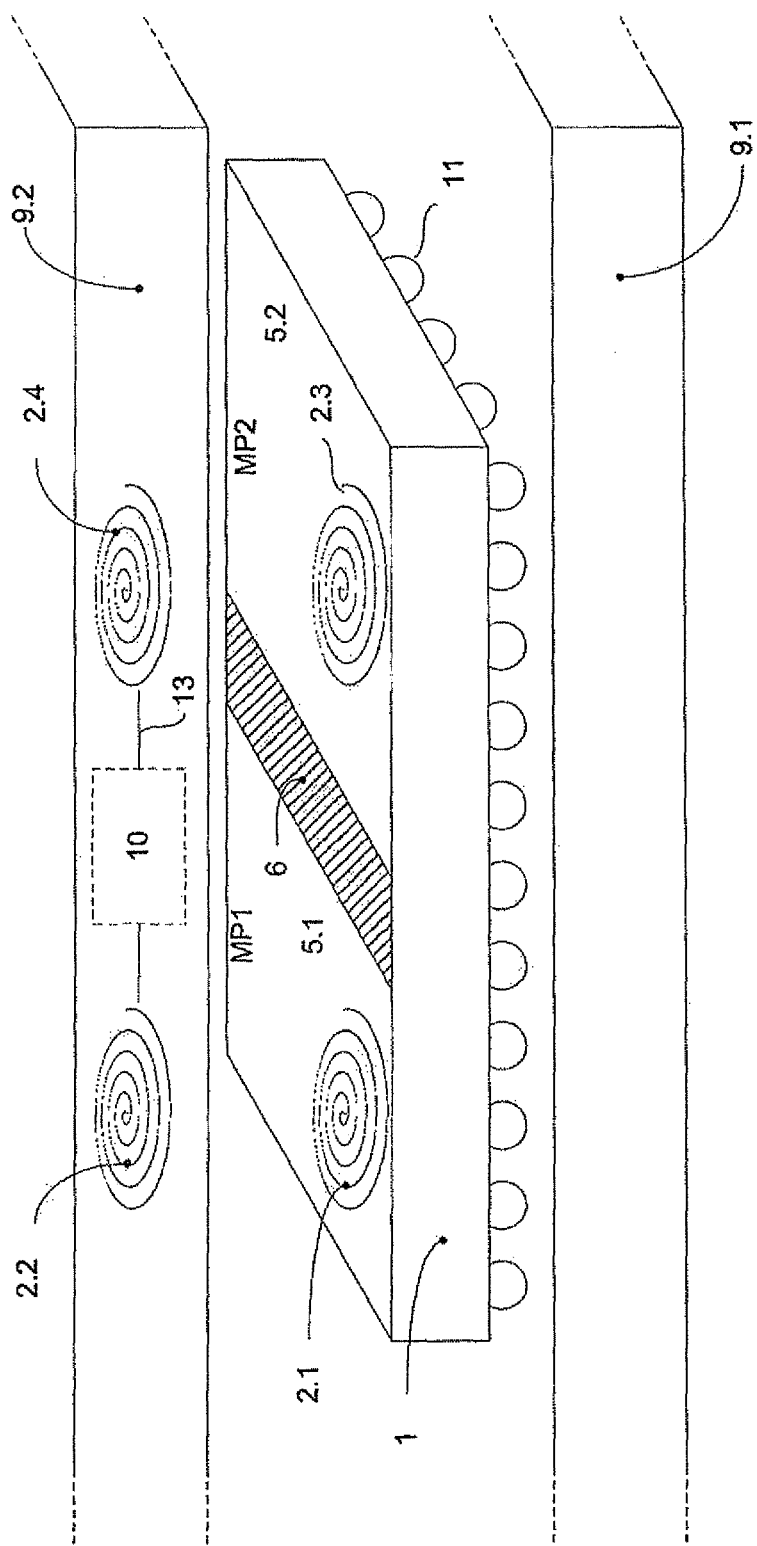
FIG. 8 is the embodiment of FIG. 7 without the magnetic field lines.

FIG. 7 shows a perspective view of a third embodiment of the FPGA component of the invention and includes the magnetic field lines. In FIG. 8, the magnetic field lines 14.1, 14.2 are, in turn, omitted. The embodiment shown in FIGS. 7 and 8 differs from the embodiment shown in FIGS. 3 and 4 by features including that the circuit board 9.2, in or on which the transmitting/receiving elements 2.3, 2.4 are arranged, is located above the FPGA component 1. The connection between the FPGA component 1 and the circuit board 9.2 occurs in the usual manner, wherein the circuit board 9.2 can indeed also be arranged spaced from the FPGA component 1.

FIG. 9 shows two arrangements of a transmitting/receiving element 2.2, 2.4 relative to the circuit board 9, 9.2. In the case of the upper embodiment, the transmitting/receiving element 2.2, 2.4 is arranged on the circuit board 9. In the case of the lower embodiment, the transmitting/receiving element 2.2, 2.4 is in the circuit board 9.

The invention claimed is:

1. A field device for determining or monitoring a physical or chemical process variable in automation technology, comprising:
   a first transmitting/receiving element in the form of a spiral;
   a second transmitting/receiving element in the form of a spiral; and
   an FPGA (Field Programmable Gate Array) component having existing internal connecting lines, wherein:
   said first transmitting/receiving element is configured in the form of said spiral from said existing internal connecting lines;

the spiral of said first transmitting/receiving element transmits data inductively to said second transmitting/receiving element;

at least a first portion and a second portion are provided on said FPGA component;

in said first portion, a first digital measuring path composed of a plurality of software based and/or hardware based, function modules is partially dynamically reconfigured;

in said second portion a second digital measuring path composed of a plurality of software based and/or hardware based function modules is partially dynamically reconfigured;

said first transmitting/receiving element in the form of a spiral is associated with the said first measuring path; and said second transmitting/receiving element in the form of a spiral is associated with said second measuring path.

2. The field device as claimed in claim 1, wherein:
said spiral of said first transmitting/receiving element is configured from said connecting lines, which are arranged in a plurality of connecting line planes of said FPGA component.

3. The field device as claimed in claim 1, wherein:
at least the spiral of said first transmitting/receiving element is configured permanently on said FPGA component; or at least the spiral of said first transmitting/receiving element is dynamically reconfigurable on said FPGA component.

4. The field device as claimed in claim 1, further comprising:
a control/evaluation unit, which partially dynamically reconfigures the function modules in said measuring paths, respectively in the portions, as a function of a defined, safety-critical application, so that the field device meets a required safety standard.

5. The field device as claimed in claim 4, wherein:
said first portion and said second portion are isolated from one another by at least one spacing.

6. The field device as claimed in claim 5, wherein:
the one or more spacings are so embodied that there is achieved between said first portion and said second portion a potential isolation in such a manner that a temperature- and/or a voltage change in one of the individual portions does not influence a neighboring individual portion, respectively the neighboring portions, and that, in the case of a defect, no connection occurs between the individual portions.

7. The field device as claimed in claim 4, wherein:
said control/evaluation unit is permanently configured in said first portion and/or a second portion of said FPGA component.

* * * * *